United States Patent [19]

Stutz, Jr.

[11] Patent Number: 5,007,864
[45] Date of Patent: Apr. 16, 1991

[54] DEVICE FOR ADAPTING A PACEMAKER LEAD TO A PACEMAKER

[75] Inventor: William H. Stutz, Jr., Burbank, Calif.

[73] Assignee: Siemens-Pacesetter, Inc., Sylmar, Calif.

[21] Appl. No.: 441,844

[22] Filed: Nov. 27, 1989

[51] Int. Cl.⁵ .......................................... H01R 25/00
[52] U.S. Cl. .................................. 439/651; 439/814; 439/177
[58] Field of Search ............... 128/783, 784, 785, 786; 439/811-814, 177, 166, 169, 170, 171, 175, 222, 651, 655, 152, 154, 483, 484, 923, 189

[56] References Cited

U.S. PATENT DOCUMENTS

| | | |
|---|---|---|
| 3,533,053 | 10/1970 | Sosinski .............................. 439/189 |
| 4,027,678 | 6/1977 | van Oostveen et al. ............. 128/419 |
| 4,236,525 | 12/1980 | Sluetz et al. ........................ 128/786 |
| 4,278,093 | 7/1981 | Lafortune et al. ................... 128/419 |
| 4,367,001 | 1/1983 | Munakata ............................ 439/175 |
| 4,628,934 | 12/1986 | Pohndorf et al. .................... 128/786 |

FOREIGN PATENT DOCUMENTS 3611865 10/1987 Fed. Rep. of Germany ...... 439/423

Primary Examiner—David L. Pirlot
Attorney, Agent, or Firm—Malcolm J. Romano; Leslie S. Miller; Lisa P. Weinberg

[57] ABSTRACT

A lead-to-pacemaker adapter allows the use of a smaller diameter lead connector than that for which the pacemaker was designed. The pacemaker is shipped with the adapter installed. If the adapter is not to be used, provision is made for its easy removal. The adapter is shown and described for use in a unipolar lead system. The adapter permits direct electrical connection from the terminal pin electrode to the pacemaker connector block and its terminal set screw without the interposition of any intermediate connecting elements.

28 Claims, 2 Drawing Sheets

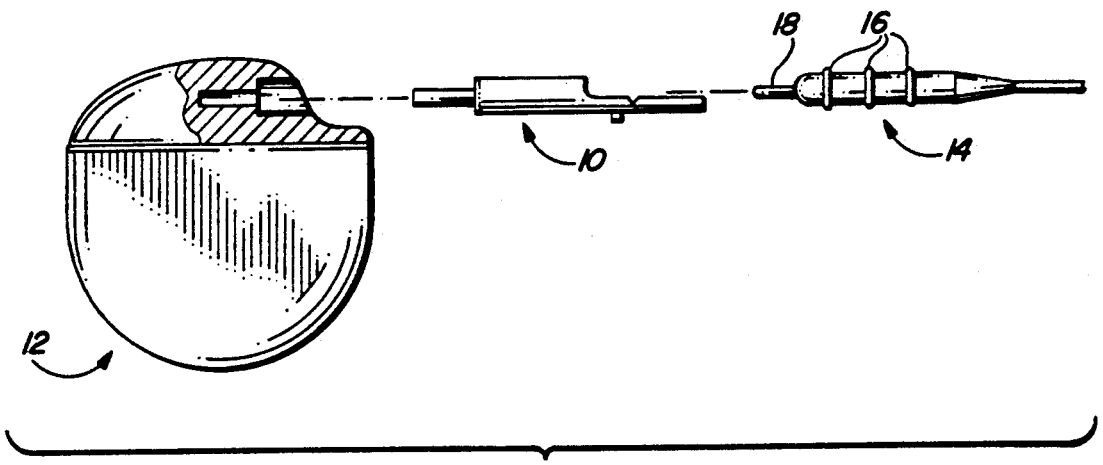
FIG-1
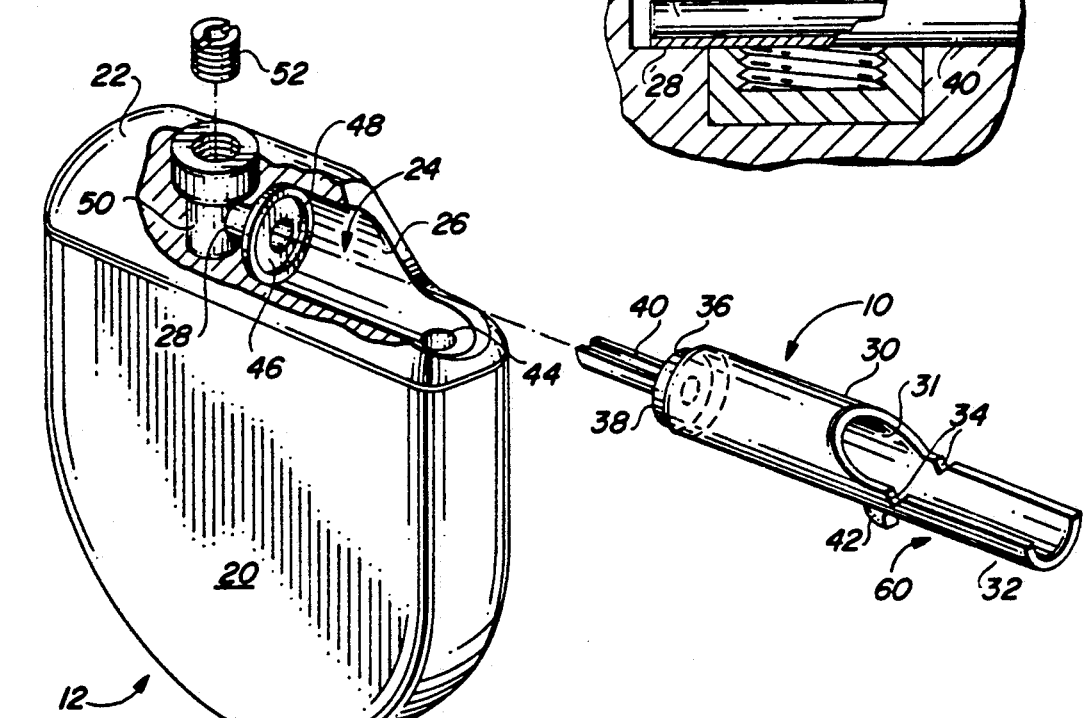
FIG-6
FIG-2

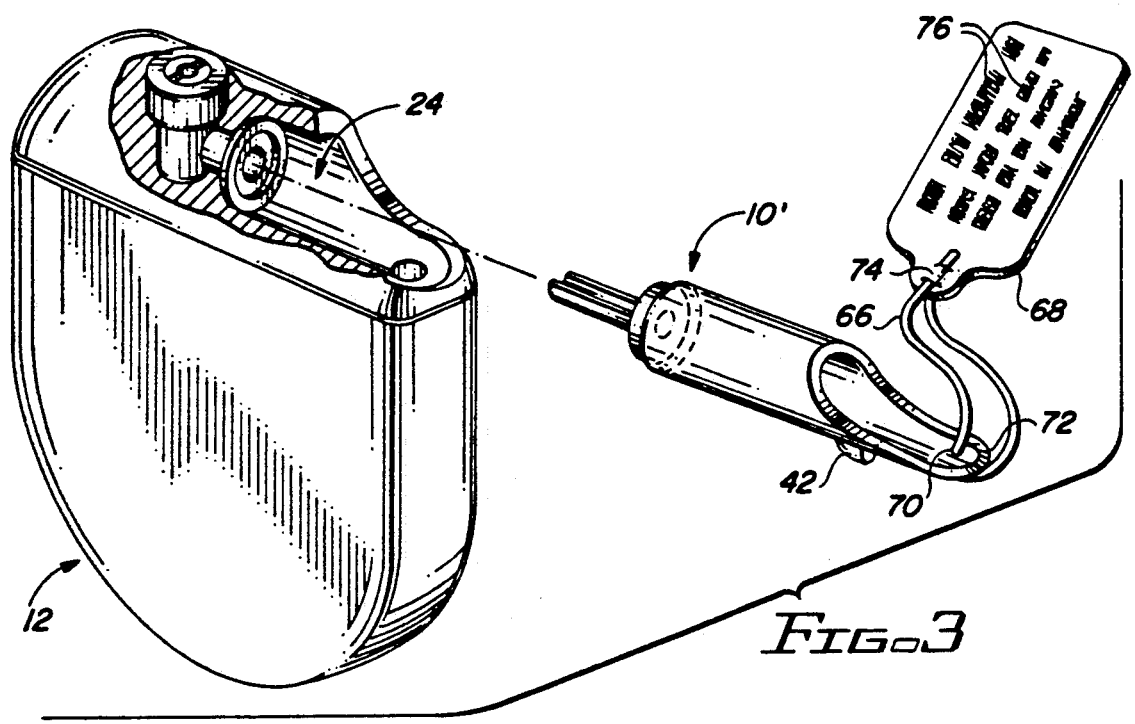
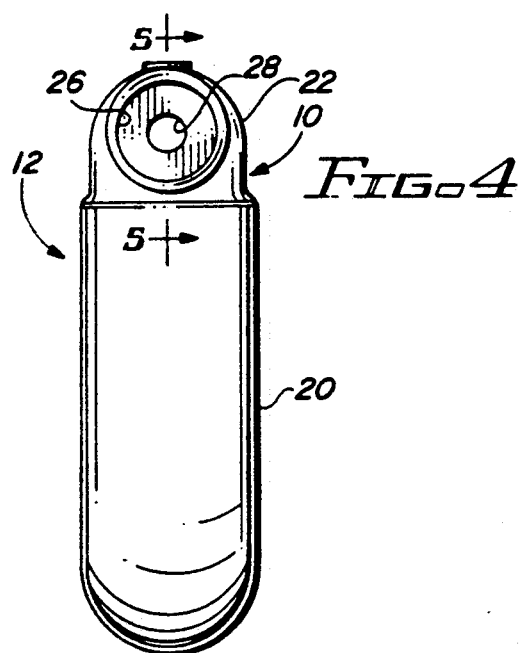
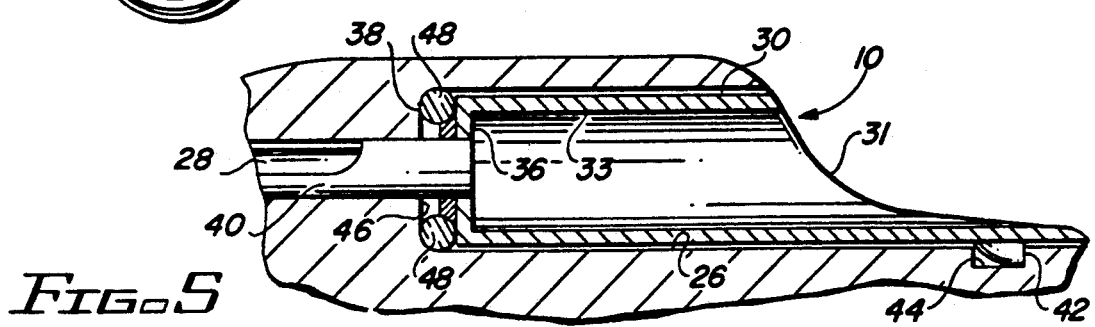

DEVICE FOR ADAPTING A PACEMAKER LEAD TO A PACEMAKER

BACKGROUND OF THE INVENTION

1. Field of the Invention

This invention relates to adapters for electrical connectors and, more particularly, to an adapter for electrically and mechanically coupling the terminal end of a pacemaker lead of one size to a pacemaker lead receptacle of another, larger size.

2. Description of the Related Art

Cardiac pacemakers, sometimes referred to as "pacemakers", are electrical devices that function to regulate the pace of the heartbeat. These vital therapeutic devices are surgically implanted in the patient's body, where they may remain for years. A typical implanted pacemaker operates by furnishing, through an electrical lead attached to the ventricle of the heart, stimulation pulses which the heart is not providing.

The pacemaker includes one or more plug-type receptacles into which the terminal electrode assembly of the electrical lead may be inserted when the pacemaker is implanted. The electrode is typically held in place in the plug receptacle of the pacemaker by a connector block and a set screw. This retaining set screw may be loosened to permit withdrawal of the terminal electrode assembly from the plug receptacle of the pacemaker, as, for example, when the pacemaker is to be replaced.

The terminal electrode assembly of the heart-stimulation leads customarily comes in different sizes. Those of more recent construction are undersized relative to earlier models. Likewise, the pacemaker receptacle which receives the terminal electrode assembly of the heart-stimulation leads comes in different sizes and varies significantly between manufacturers. In view of the fact that the installed heart-stimulation lead generally lasts longer than the cardiac pacemaker, it would be advantageous to be able to re-use the lead by adapting it to any given pacemaker model, independent of the particular size jack for the heart lead terminal electrode assemblies. This goal can be achieved by providing an adapter which is of the proper size to plug into the pacemaker receptacle and at the same time receive the implanted lead terminal electrode in a manner which establishes a reliable mechanical and electrical connection between the lead and the pacemaker.

One such adapter is disclosed in U.S. Pat. No. 4,583,543 of Peers-Trevarton. The device of that patent, however, is relatively complex in structural design, constituting a separate receptacle for the undersized terminal electrode assembly of the heart lead and a corresponding separate adapter terminal electrode assembly to couple into the full size pacemaker jack. Essentially, the adapter is constructed with the portion which couples to the pacemaker being configured like the large size terminal electrode assembly for which the pacemaker is designed.

What is presently desired is a simplified adapter which provides a match between the disparate sizes of the lead terminal electrode assembly and the pacemaker receptacle while facilitating the integrity of the connection between the pacemaker receptacle and the undersized terminal electrode assembly of the heart lead. The adapter of the present invention fulfills this need as a device which is easier and more economical to manufacture than those which are known in the prior art, as well as being at least as reliable in use.

SUMMARY OF THE INVENTION

In brief, arrangements in accordance with the present invention are in the form of a generally cylindrical, tubular sleeve having outer diameter dimensions matching the inner diameter dimensions of the pacemaker jack and inner diameter dimensions matching the outer diameter dimensions of a smaller size (undersized) terminal electrode assembly, including the axial pin electrode, of an implanted heart lead. For example, the diameter of the pacemaker receptacle may be 6 millimeters while the outer diameter of the lead connector is 3.2 millimeters. The outer diameter of the adapter of the present invention is then nominally 6 millimeters, to fit within the 6-millimeter inner diameter of the pacemaker receptacle, while the inner diameter of the adapter of the present invention is nominally 3.2 millimeters so as to receive the undersized terminal electrode assembly with the same fit and support that would be afforded if the pacemaker were manufactured to fit a terminal electrode assembly of 3.2 millimeter size.

In accordance with an aspect of the invention, the adapter is formed with a protruding bump strategically located to snap into a hole or recess near the entrance of the pacemaker receptacle bore in order that the adapter may be retained in the pacemaker head by latching it in place for use. It is contemplated that the adapter will be installed in the pacemaker when it is shipped from the factory. The adapter is retained in position until the pacemaker is unpacked for ultimate use. In case the pacemaker is to be used with a full size terminal electrode assembly of mating dimensions, in which event the adapter is not needed, the adapter is provided with means to facilitate its removal from the pacemaker. In one exemplary embodiment, this removal mechanism is in the form of an extending tab which can be used to disengage the latching protrusion from the pacemaker receptacle and pull the adapter out of the receptacle for ready removal and disposition. In another exemplary embodiment, the removal mechanism is a flexible ring with a tag attached. This tag may bear suitable indicia in the form of instructions as to how the adapter may be used or removed, and it also serves as a handle which may be used to draw the ring taut in disengaging the adapter from the pacemaker receptacle.

In one particular arrangement, an 0-ring is provided to fit between the inner end face of the adapter and the inner end face of the pacemaker receptacle bore. This 0-ring effectively serves as a seal by being brought under compression when the adapter is snapped into place and held by the latching mechanism.

BRIEF DESCRIPTION OF THE DRAWINGS

A better understanding of the present invention may be realized from a consideration of the following detailed description, taken in conjunction with the accompanying drawing in which:

FIG. 1 is a schematic diagram indicating how the adapter of the present invention is used in conjunction with a pacemaker having a jack of one size and a heart lead terminal electrode assembly of a different, smaller size;

FIG. 2 is a perspective view, partially broken away, indicating how the adapter is positioned within the pacemaker receptacle;

FIG. 3 is a view similar to that of FIG. 2, showing an alternative embodiment of the adapter;

FIG. 4 is an end view of a pacemaker showing an adapter of the present invention in position within the pacemaker receptacle;

FIG. 5 is an enlarged view of the upper portion of the pacemaker of FIG. 4, partially broken away to show a sectional view taken along the line 5—5 of FIG. 4; and FIG. 6 is a further enlarged view showing details of the connector block and set screw that comprise that portion of the jack used to retain the heart lead pin electrode.

DESCRIPTION OF THE PREFERRED EMBODIMENTS

As indicated in the schematic exploded view of FIG. 1, an adapter 10 of the present invention is shown in juxtaposition between a pacemaker 12 having a large or full size receptacle or jack and an undersized terminal electrode assembly 14. As better shown in FIG. 2, the pacemaker 12 has a main body portion 20 and a head portion 22. The head portion 22 is fashioned with a jack 24 comprising a main receptacle portion 26 and a pin receptacle portion 28. The main receptacle portion 26 is adapted to receive the proximal end of a full size terminal electrode assembly while the pin receptacle portion 28 receives the pin electrode extending from either a full-sized or an undersized terminal electrode assembly. The smaller size terminal lead assembly 14 is of the unipolar type and is exactly like the full size terminal lead assembly for which the pacemaker 12 with jack 24 is designed. As described and claimed herein, the smaller size terminal electrode assembly will be referred to as "undersized". This should be understood as referring to an electrode assembly like that for which the jack is designed, but smaller in size and unable to couple properly with the jack without some sort of adaptor. The terminal electrode assembly 14 is shown with a pin electrode 18 and three sealing rings 16 which are designed to seal the main receptacle portion of the pacemaker jack in which it is inserted.

The adapter 10 is generally tubular in shape and includes a generally cylindrical body 30 which tapers at the open end to an extension 32. A pair of notches 34 are located between the extension 32 and the body 30, the purpose of which will be described below. The adapter 10 is preferably injection molded of a rigid biocompatible plastic which is transparent, such as the material sold under the trademark Polysulfone by Amoco. It is closed at the distal end 36 defining an end face 38 from which an electrically conductive shell portion 40 in the form of a half-round tube extends outwardly. The shell portion 40 is a separate metallic member which is molded as part of the adapter 10 during the molding process.

The adapter 10 has on its underside a retaining bump 42 provided for latching the adapter 10 in place within the jack 24. The main receptacle portion 26 of the jack 24 has a small hole or recess 44 near the outer opening thereof along its bottom side. When the adapter 10 is inserted in place within the jack 24, the retaining bump 42 engages within the recess 44, as best shown in FIG. 5.

The inner end face 46 of the jack 24 is generally planar and orthogonal to the axis of the main receptacle portion 26. An O-ring 48 is installed adjacent the inner end face 46 prior to positioning of the adapter 10 in place within the jack 24. As indicated in FIG. 5, the O-ring 48 is compressed between the end face 38 of the adapter 10 and the inner end face 46 of the main receptacle portion 26 when the adapter 10 is inserted far enough for the retaining bump 42 to latch within the recess 44. This latching mechanism maintains the compression of the O-ring 48, thereby establishing an effective fluid seal between the adapter 10 and the inner end face 46 of the main receptacle portion 26.

As shown in FIGS. 5 and 6, the shell portion 40 extends into the pin receptacle portion 28 of the jack 24. FIG. 6 shows an enlarged view of the arrangement for retaining the terminal electrode assembly 14 in firm mechanical and electrical coupling to the pacemaker 12. That pin electrode 18 is electrically connected to an internally threaded metal connector block 50 which is part of the head portion 22 of the pacemaker 12. A socket recess set screw 52 is threaded into a connector block 50 until the flat tip of the set screw 52 contacts the pin electrode 18. Because the shell portion 40 is open at the top, this contact is established directly between the pin electrode 18 and the set screw 52, as well as the underside of the shell portion 40 and the connector block 50, just as though the pin electrode of a larger size terminal electrode assembly were inserted directly into the jack 24 without the interposition of an adapter. The shell portion 40 serves to provide support on the underside for the pin electrode 18, such that no axial misalignment occurs when the set screw 52 is tightened, thus maintaining the integrity of the lead seal within the adapter. Thus, the electrical connection of the pin electrode 18 of the terminal electrode assembly 14 via the connector block 50 and set screw 52 is exactly the same as if no adapter were involved, considering that a full size assembly would be used. This circuit connection does not depend upon any other electrically conducting elements of an adapter for its circuit integrity, as do some of the known prior art adapters which serve a similar function.

The pacemaker is intended to be shipped from the factory with the adapter 10 installed. A removal tab 60, which is formed by the extension 32 (FIG. 2), serves to facilitate withdrawal of the adapter 10 if the physician elects to use the original larger size jack 24 of the pacemaker 12 directly with a full size terminal lead assembly. If the adapter 10 needs to be removed when the pacemaker 12 is to be installed, the outer end of the adapter 10 is flexed slightly by lifting on the removal tab 60, lifting the retaining bump 42 out of the recess 44 and withdrawing the adapter 10 from the jack 24. Conversely, if the adapter 10 is to be used in the coupling of an undersized terminal electrode assembly into the jack 24, the removal tab 60 is flexed manually at the notches 34 and broken off at that point, leaving the adapter 10 captive and free of any extension beyond the open end of the main receptacle portion 26.

FIG. 3 shows an adapter 10' for insertion in the jack 24 of a pacemaker 12. The only difference between the adapter 10' of FIG. 3 and the adapter 10 of FIG. 2 is the mechanism which is provided for withdrawing the adapter from the jack 24 if it is not to be used. Instead of the detachable extension 32 of FIG. 2, a thin flexible plastic lanyard 66 is shown extending from a tag 68 through a small hole 70 in an end 72 of the adapter 10'. After threading the hole 70, the lanyard 66 is returned to the tag 68 where it is gripped by a clamp 74. The tag 68 may be provided with indicia 76 in the form of text or graphics which may serve as identification of the model of the pacemaker 12, instructions for use including removal of the adapter 10', or any other information which is desired.

With the arrangement of FIG. 3, if the adapter 10' is to be used in the jack 24 of the pacemaker 12, the lanyard 66 is simply cut and the tag 68 with the severed lanyard 66 is withdrawn and discarded. Conversely, if the adapter 10' is to be removed from the jack 24 of the pacemaker 12, the tag 68 and lanyard 66 are used as a handle to flex the outer end of the adapter 10' sufficiently to withdraw the retaining bump 42 from the recess 44 and then withdraw the adapter 10' from the jack 24 of the pacemaker 12.

Thus, arrangements in accordance with the present invention provide an improved adapter for accommodating an undersized pacemaker lead terminal electrode assembly and a pacemaker having a jack which is designed for a full size terminal electrode assembly. The adapter is preferably formed of plastic by injection molding, is economical and simple to manufacture and achieves a high integrity electrical and mechanical connection between the terminal electrode assembly and the pin retaining mechanism within the pacemaker. With the adapter in position within the pacemaker, an effective fluid seal is established from the terminal electrode assembly to the interior surface of the adapter and from the outer end of the adapter to the end of the pacemaker main receptacle, thereby protecting the electrical circuit connection between the terminal pin electrode and the internal pacemaker lead connector from the environment. The adapter is latched in position within the pacemaker jack by a simple latching mechanism which also prevents the adapter from rotating within the pacemaker, thus positioning the pin adapter properly so that the pacemaker set screw clamps the pin electrode effectively. The adapter is designed to be installed in the pacemaker when shipped from the factory and is provided with a simple means for withdrawing the adapter from the pacemaker jack in the event that it is determined that the adapter is not needed when the pacemaker is installed.

Although there have been described hereinabove specific arrangemens of a device for adapting a pacemaker lead to a pacemaker in accordance with the invention for the purpose of illustrating the manner in which the invention may be used, it will be appreciated that the invention is not limited thereto. Accordingly, any and all modifications, variations or equivalent arrangements which may occur to those skilled in the art should be considered within the scope of the invention as defined in the appended claims.

What is claimed is:

1. An adapter for use in a coping a generally cylindrical terminal electrode assembly to a device having a jack for receiving the assembly, the terminal electrode assembly being undersized relative to the dimensions of the jack, the adapter comprising:
   a thin-walled tubular portion defining a hollow bore terminating in an end wall at a distal end thereof and an entry opening at a proximal end thereof, the outer diameter of the tubular portion being selected to match the inner diameter of the jack, the diameter of the tubular portion being selected to match the outer diameter of the terminal electrode assembly;
   means for releasably latching the adapter within the jack of the device;
   means for releasing the latching means and withdrawing the adapter from the jack, wherein the releasing and withdrawing means is detachable from the adapter; and
   wherein the releasing and withdrawing means further comprises:
      a tab extending from one side of the tubular portion outwardly past the entry opening; and
      means defining a pair of notches located to establish a separation point to facilitate breaking off the tab from the tubular portion.

2. The adapter of claim 1, wherein the device is a pacemaker and the terminal lead assembly is connected to a heart stimulation lead.

3. The adapter of claim 1, wherein the releasing and withdrawing means comprises a severable lanyard and a tag linked to the tubular portion by the severable lanyard, the tubular portion having a hole at one end, the severable lanyard extending through the hole in the tubular portion and being attached to the tag.

4. The adapter of claim 3, wherein the tag is provided with indicia constituting instructions for use.

5. The adapter of claim 1, wherein the terminal electrode assembly includes a plug body having a pin electrode extending therefrom, and the jack includes a main receptacle portion for receiving the plug body and a pin electrode bore for receiving the pin electrode of the terminal electrode assembly, both the plug body and the pin electrode being undersized relative to the main receptacle portion and the pin electrode bore of the jack, the adapter further comprises:
   end wall means defining an opening to permit the pin electrode of the terminal electrode assembly to pass through the end wall into the pin electrode bore.

6. The adapter of claim 5, wherein the plug body comprises a plurality of annular sealing rings and wherein the inner surface of the tubular portion is shaped to establish a seal with the sealing rings when the terminal electrode assembly is installed within the adapter in the jack.

7. The adapter of claim 5, wherein the device further comprises means for releasably gripping the pin electrode to retain the terminal electrode assembly within the jack.

8. The adapter of claim 7 further comprising a half-round electrically conductive tube extending beyond the end wall means for insertion into the pin electrode bore to provide support for the pin electrode when the pin electrode is clamped within the pin electrode bore by the gripping means.

9. The adapter of claim 8, wherein the gripping means comprises a set screw adapted to clamp the pin electrode within the pin electrode bore, and wherein the half round tube is adapted to cradle the pin electrode and establish a fit for the pin electrode within the pin electrode bore while enabling the set screw to clamp directly to the pin electrode.

10. The adapter of claim 9, wherein the tubular portion is a molded plastic tubular portion and the half-round tube is a stainless steel half-round tube integrally installed in the end wall means.

11. The adapter of claim 10, wherein the device is a heart pacemaker, and the terminal electrode assembly is part of a heart stimulation lead.

12. The adapter of claim 8, wherein the latching means comprises a retaining bump protruding outwardly from the tubular portion in the vicinity of the entry opening, and the jack comprises the means for engaging the retaining bump near the entry opening when the adapter is positioned within the jack.

13. The adapter of claim 12, wherein the retaining bump is oriented radially outward relative to the half-round tube, such that the half-round tube is located within the pin electrode bore on the side opposite the set screw when the retaining bump is latched within the engaging means of the jack.

14. The adapter of claim 13, wherein the jack has a generally planar transverse wall at an inner end of the jack, and the adapter end wall is generally planar and transverse to the longitudinal axis thereof, further comprising sealing means for providing a seal between the adapter and the jack.

15. The adapter of claim 14, wherein the sealing means comprises an O-ring installed adjacent the inner end wall of the jack, the adapter being effective to compress the O-ring to develop the seal when the retaining bump is engaged within the engaging means, thereby latching the adapter within the jack.

16. An adapter for use in coupling a terminal electrode assembly including a plug to a device having a jack for receiving the plug for electrical connection thereto, the plug having a lead pin of a first diameter extending from a plug body having a second diameter substantially larger than the first diameter, the jack including a lead pin receptacle having a third diameter designed to receive a lead pin of a size larger than the first diameter, a main receptacle portion having a fourth diameter designed to receive a plug of a size larger than the second diameter, and an electrode for making electrical contact between the lead pin and the device, the adapter comprising:

a generally cylindrical, thin-walled tubular portion defining an end wall at a first end and an entry opening at a second end of the tubular portion, the end wall having an opening matching the first diameter for permitting the lead pin to pass therethrough for connecting to the electrode of the jack when the adapter is inserted in position within the main receptacle portion and the plug body is inserted within the tubular portion.

17. The adapter of claim 16 further comprising means for releasably latching the adapter in position within the jack.

18. The adapter of claim 17, wherein the latching means comprises:

a engaging means near the entrance of the jack; and a protruding member extending radially outward from the tubular portion near the entry opening thereof, the length of the tubular portion between the end wall and the protruding member being preselected to match the length of the main receptacle portion between the inner end thereof and the engaging means in order to establish an end wall seal between the jack and the adapter.

19. The adapter of claim 18 further comprising resilient sealing means located between the inner end of the main receptacle portion and the end wall of the adapter in a position to be compressed by the latching of the adapter within the jack.

20. The adapter of claim 19, wherein the sealing means comprises an O-ring.

21. The adapter of claim 16, wherein the wall thickness of the tubular portion is selected to substantially fill the circumferential space between the plug body and the main receptacle portion.

22. The adapter of claim 21, wherein the inner diameter of the tubular portion is nominally equal to the second diameter, and the outer diameter of the tubular portion is nominally equal to the fourth diameter.

23. The adapter of claim 22 further comprising:

a set screw for releasably gripping the lead pin; and a half-round tube extending axially from the end wall and defining an opening therein, the half-round tube being radially oriented to support the lead pin when the lead pin is clamped by the set screw.

24. The adapter of claim 17 further comprising removable means for withdrawing the adapter from its latched position within the jack.

25. The adapter of claim 24, wherein the removable means comprises a tab extending from the tubular portion at one side thereof, the tab being notched to define a break point for detachment of the tab from the tubular portion.

26. The adapter of claim 23, wherein the half-round tube is selectively dimensioned to fill one-half the space between the lead pin and the lead pion receptacle, thus preventing axial displacement of the lead pin when the set screw is tightened.

27. The adapter of claim 26, wherein the inner diameter of the half-round tube is nominally equal to the first diameter, and the outer diameter of the half-round tube is nominally equal to the third diameter.

28. The adapter of claim 26, wherein the removable means comprises a tag attached to the adapter by a severable link.

* * * * *